(12) United States Patent
Kurosaki (10) Patent No.: US 6,540,680 B1
(45) Date of Patent: Apr. 1, 2003

(54) ULTRASONIC DIAGNOSTIC APPARATUS

(75) Inventor: Tatsuru Kurosaki, Nasu-gun (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/685,084

(22) Filed: Oct. 11, 2000

(30) Foreign Application Priority Data

Oct. 15, 1999 (JP) .............................................. 11-294252

(51) Int. Cl.$^7$ ................................................ A61B 8/00

(52) U.S. Cl. ........................ 600/443; 600/458; 600/462

(58) Field of Search ................................ 600/462, 439, 600/458, 466, 467, 437, 443, 358; 378/8, 69; 604/65; 368/101

(56) References Cited

U.S. PATENT DOCUMENTS

| | | | | | |
|---|---|---|---|---|---|
| 4,396,296 | A | * | 8/1983 | Stodden | 368/101 |
| 4,504,263 | A | * | 3/1985 | Steuer et al. | 128/DIG. 13 |
| 5,224,481 | A | * | 7/1993 | Ishihara et al. | 600/443 |
| 5,583,902 | A | * | 12/1996 | Bae | 378/8 |
| 5,749,361 | A | * | 5/1998 | Mateyko | 600/437 |
| 6,144,875 | A | * | 11/2000 | Schweikard et al. | 378/69 |

* cited by examiner

Primary Examiner—Marvin M. Lateef
Assistant Examiner—Ruby Jain
(74) Attorney, Agent, or Firm—Oblon, Spivak, McClelland, Maier & Neustadt, P.C.

(57) ABSTRACT

An ultrasonic image diagnostic apparatus measures an arbitrary elapsed time in an arbitrary time measuring circuit, and simultaneously displays this time information and an ultrasonic image on a monitor or stores the image and the elapsed time information in a storage section in correspondence with each other.

10 Claims, 5 Drawing Sheets

ULTRASONIC DIAGNOSTIC APPARATUS

CROSS-REFERENCE TO RELATED APPLICATIONS

This application is based upon and claims the benefit of priority from the prior Japanese Patent Application No. 11-294252, filed Oct. 15, 1999, the entire contents of which are incorporated herein by reference.

BACKGROUND OF THE INVENTION

The present invention relates to an ultrasonic image diagnostic apparatus having a time measuring function capable of measuring an arbitrary time.

An ultrasonic image diagnostic apparatus is a diagnostic apparatus for irradiating a desired region in an object (patient) with an ultrasonic wave and obtaining a tomographic image of a soft tissue on the basis of a reflected wave from the inside of the object. The physical quantity handled by this ultrasonic image diagnostic apparatus is ultrasonic waves. Owing to this characteristic feature, this apparatus is safer than other medical diagnostic equipment, and has various characteristic features in imaging forms and display forms.

In diagnosis by this ultrasonic image diagnostic apparatus, it is important in some case to grasp a predetermined elapsed time. A diagnostic method using an ultrasonic contrast medium will be described below as an example of this case.

Figure 1:
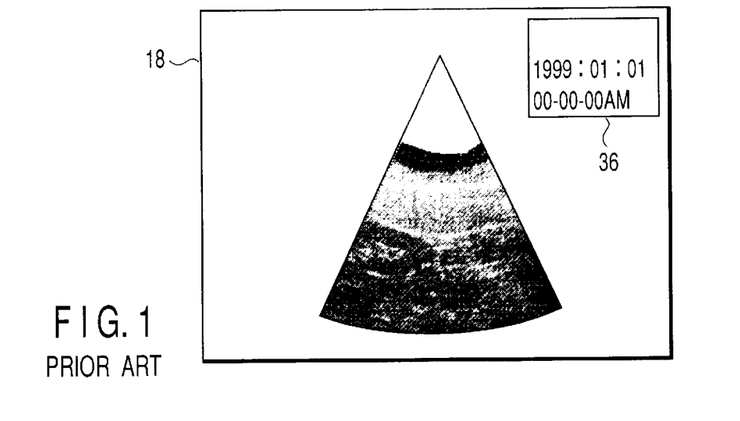
FIG. 1 is a view for explaining a prior art.

The diagnostic method using an ultrasonic contrast medium aims to enhance the reflection of ultrasonic waves, make ultrasonic images clearer, and improve the diagnosis ability by administering a contrast medium such as bubbles having an acoustic impedance different from that of blood into a vein or the like in an object. In imaging an ultrasonic image by using this contrast medium, it is important to grasp an elapsed time, e.g., the time interval between the instant at which the contrast medium is administered and the instant at which the contrast medium flows into a desired object to be imaged. In a prior art, operation is performed while an administration start time or an elapsed time from the start of administration is grasped by using a date display 36 provided on the monitor of the ultrasonic image diagnostic apparatus shown in FIG. 1 or an external timepiece prepared separately.

In a method of imaging an object to be displayed and checking its function over time by applying a stress caused by a drug as well, similar time grasping operation is performed.

As described above, when an elapsed time is to be graphed by using a timepiece provided for the apparatus or an external timepiece in imaging operation for an ultrasonic image, in which a predetermined elapsed time must be graphed, an administration time and imaging time must always be grasped. This imposes a large load on the operator. When the external timepiece is to be used, in particular, time information must be stored independently of image information obtained by the above imaging method, resulting in a considerable deterioration in operability.

BRIEF SUMMARY OF THE INVENTION

The present invention has been made in consideration of the above situation, and has as its object to provide an ultrasonic image diagnostic apparatus which can easily grasp an elapsed time in ultrasonic image diagnosis in which a predetermined elapsed time needs to be grasped. This apparatus has the following characteristic features.

According to the first aspect of the present invention, there is provided an ultrasonic diagnostic apparatus comprising means for generating an ultrasonic image by scanning the inside of an object with an ultrasonic wave, and a stopwatch for measuring an arbitrary time in ultrasonic diagnosis.

According to the present invention associated with the first aspect, since an arbitrary elapsed time can be measured in ultrasonic diagnosis, the cumbersome operation of separately calculating an elapsed time can be omitted, and the operability can be improved.

According to the second aspect of the present invention, there is provided an ultrasonic diagnostic apparatus comprising means for generating an ultrasonic image by scanning the inside of an object with an ultrasonic wave, means for obtaining an elapsed time from a predetermined time or generating information from which the elapsed time can be derived, and means for linking the elapsed time or the information from which the elapsed time can be derived to the ultrasonic image.

According to the present invention associated with the second aspect, since an ultrasonic image and an elapsed time or information from which the elapsed time can be derived can be simultaneously displayed, an observer can easily grasp the elapsed time and the like. This makes it possible to omit the cumbersome operation of separately calculating an elapsed time and improve the operability.

According to the third aspect of the present invention, there is provided an ultrasonic diagnostic apparatus comprising means for generating an ultrasonic image by scanning the inside of an object with an ultrasonic wave, means for obtaining an elapsed time from a predetermined time or generating information from which the elapsed time can be derived, and means for linking the elapsed time or the information from which the elapsed time can be derived to function information of the object.

According to the present invention associated with the third aspect, since the elapsed time or the information from which the elapsed time can be derived can be linked to the function information of the object, the observer can easily grasp the elapsed time and the like. This makes it possible to omit the cumbersome operation of separately calculating an elapsed time and improve the operability.

The following are the preferred embodiments of the ultrasonic diagnostic apparatus according to the present invention.

(1) In the ultrasonic image diagnostic apparatus according to the second or third aspect, the predetermined time is preferably during administration of an ultrasonic contrast medium. The predetermined time if may be during input of the information about the object. Moreover, in the ultrasonic image diagnostic apparatus according to the second or third aspect, when the ultrasonic diagnostic apparatus obtains information associated with a new object, the means for obtaining the elapsed time or the generating information starts, after resets, to obtain a new elapsed time from a predetermined time point or new generating information from which the new elapsed time can be derived.

According to this arrangement, the observer can easily grasp an elapsed time from contrast medium administration. If, for example, the information about the object is a patient ID, an elapsed time of diagnosis on a specific patient can be easily grasped. In addition, time measurement is reset every time a patient ID is input. This can prevent operation errors.

(2) It is preferable that the ultrasonic diagnostic apparatus according to the second aspect further comprise display means for simultaneously displaying the linked elapsed time or the linked information from which the elapsed time can be derived and the ultrasonic image or the function information of the object.

According to this arrangement, since an ultrasonic image or the function information of the object and an elapsed time from the point of time at which an ultrasonic contrast medium is administered or information from which the elapsed time can be derived can be simultaneously displayed, the observer can easily grasp the elapsed time and the time. This makes it possible to omit the cumbersome operation of separately calculating an elapsed time and improve the operability.

(3) It is preferable that the ultrasonic diagnostic apparatus according to the second aspect further comprise means for storing the linked elapsed time or the linked information from which the elapsed time can be derived and the ultrasonic image or the function information of the object in correspondence with each other. This apparatus may further comprise means for storing an image obtained by synthesizing the ultrasonic image and the function information of the object into one frame.

According to arrangement, since an ultrasonic image or the function information of the object and an elapsed time can be stored while they are linked to each other, the observer can easily grasp an elapsed time even when, for example, an ultrasonic image is reconstructed. This makes it possible to omit the cumbersome operation of separately calculating an elapsed time and improve the operability.

(4) The ultrasonic diagnostic apparatus according to the second aspect may further comprise means for synchronizing control associated with a start, pause, and stop of measurement of the elapsed time or the information from which the elapsed time can be derived with control associated with imaging or storage of an ultrasonic image.

According to this arrangement, since control associated with the start, pause, and stop of time measurement can be synchronized with control associated with imaging or storage of an ultrasonic image, the operation associated with time measurement can further simplified. This improves the operability.

(5) The ultrasonic diagnostic apparatus according to the second aspect may further comprise means for synchronizing control associated with a start, pause, and stop of measurement of the elapsed time or the information from which the elapsed time can be derived with control associated with an external device.

According to this arrangement, since control associated with the start, pause, and stop of time measurement is synchronized with control for an external device, the operation associated with time measurement can be further simplified. This improves the operability.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

The first to fifth embodiments of the present invention will be described with reference to the views of the accompanying drawing. Note that the same reference numerals in the following description denote the same parts, and a repetitive description will be made only when necessary.

(First Embodiment)

Figure 2:
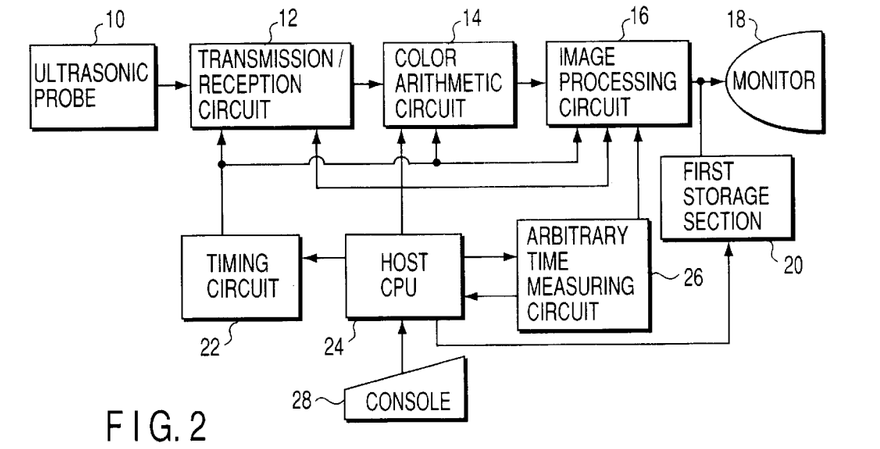
FIG. 2 is a block diagram showing the schematic arrangement of an ultrasonic image diagnostic apparatus according to the first embodiment.

FIG. 2 shows the schematic arrangement of an ultrasonic image diagnostic apparatus.

Referring to FIG. 2, an ultrasonic image diagnostic apparatus 1 includes an ultrasonic probe 10, transmission/reception circuit 12, color arithmetic circuit 14, image processing circuit 16, monitor 18, first storage section 20, timing circuit 22, host CPU 24, arbitrary time measuring circuit 26, and console 28.

The ultrasonic probe 10 is a probe for irradiating the inside of an object (patient) with an imaging ultrasonic wave. This probe is formed by using a piezoelectric element.

The transmission/reception circuit 12 is a circuit for irradiating the inside of the object with an electrical signal as a sound wave and receiving a reflected sound wave from the object. The electrical signal of the received sound wave is A/D-converted and sent to the color arithmetic circuit 14.

The color arithmetic circuit 14 detects the phase of the digital signal from the transmission/reception circuit 12 to obtain a Doppler shift signal, and performs color processing for the signal.

The image processing circuit 16 writes the image signal from the color arithmetic circuit 14 and a time signal from the arbitrary time measuring circuit 26 (to be described later) in an image memory, and performs TV scan conversion of the signals. The image processing circuit 16 then sends out the resultant signals to the monitor 18. The image processing circuit 16 also executes image processing such as multiple focusing, freezing, a post process, and a γ process.

The image processing circuit 16 plots changes in luminance in an area of interest over time on the basis of input image signals. This graph is called a TIC (Time Intensity Curve) and used to quantitatively grasp the process of intensifying an echo signal in the area of interest.

The monitor 18 displays an image (to be referred to as a "frame image" hereinafter) obtained by synthesizing the ultrasonic image input from the image processing circuit 16 with the time measured by the arbitrary time measuring circuit 26 within a single frame.

The first storage section 20 is a storage section for storing a desired frame image displayed on the monitor 18. This frame image is assigned a patient ID or the like and managed in accordance with the corresponding number or the like.

The timing circuit 22 sends out a control signal for controlling the scan timing and the number of scan operations in accordance with an imaging mode to the color arithmetic circuit 14 and image processing circuit 16.

The host CPU 24 is a control section for performing control associated with imaging operation and time measurement accompanying the imaging operation. The host CPU 24 also performs image capture control in accordance with an image capture input (to be described later).

The arbitrary time measuring circuit 26 has a stopwatch function and can measure an arbitrary time accompanying imaging operation (e.g., an elapsed time from contrast medium administration to imaging operation). As will be described in detail later, the arbitrary time measuring circuit 26 performs time measurement accompanying imaging operation and sends out time information about the resultant image to the image processing circuit 16.

The console 28 is an interface constituted by a keyboard, mouse, and the like and is used by an operator to perform a series of operations associated with arbitrary time measurement accompanying imaging operation.

Imaging operation performed by the ultrasonic image diagnostic apparatus 1 having the above arrangement using a flash echo imaging method will be described next. The flash echo imaging method is an imaging method of administering a contrast medium or a drug or the like serving as a stress into the object while observing ultrasonic images in real time, and capturing (storing) desired ultrasonic images over time. In this imaging method, it takes time for, for example, a contrast medium to flow into a desired organ or the like, and it is important to check how the contrast medium or the like moves the desired organ over time. It is therefore significant to grasp an elapsed time.

Figure 3:
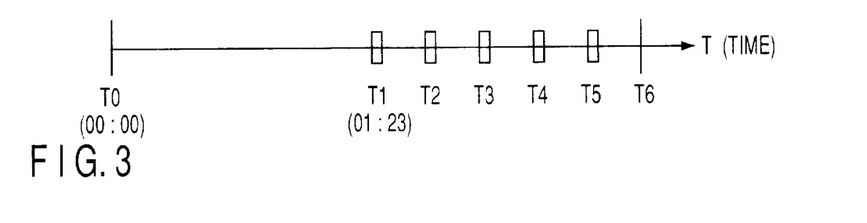
FIG. 3 is a view for explaining imaging operation based on a flash echo imaging method.

FIG. 3 is a view for explaining imaging operation performed by the ultrasonic image diagnostic apparatus 1 using the flash echo imaging method in accordance with the time measured by the arbitrary time measuring circuit 26. Operation to be performed when the operator manually executes arbitrary time measurement will be described below.

The operator performs input operation using the console 28 to start time measurement at the same timing as that of the administration of a contrast medium into the object. In general, this time measurement is started at the same timing as that of contrast medium administration. However, this operation may be started at a desired timing as long as the operator can grasp an elapsed time.

The arbitrary time measuring circuit 26 starts time measurement in accordance with the above input operation. The measured time is always sent out to the image processing circuit 16 and displayed as an elapsed time from contrast medium administration on the monitor 18, together with an ultrasonic image.

Figure 4:
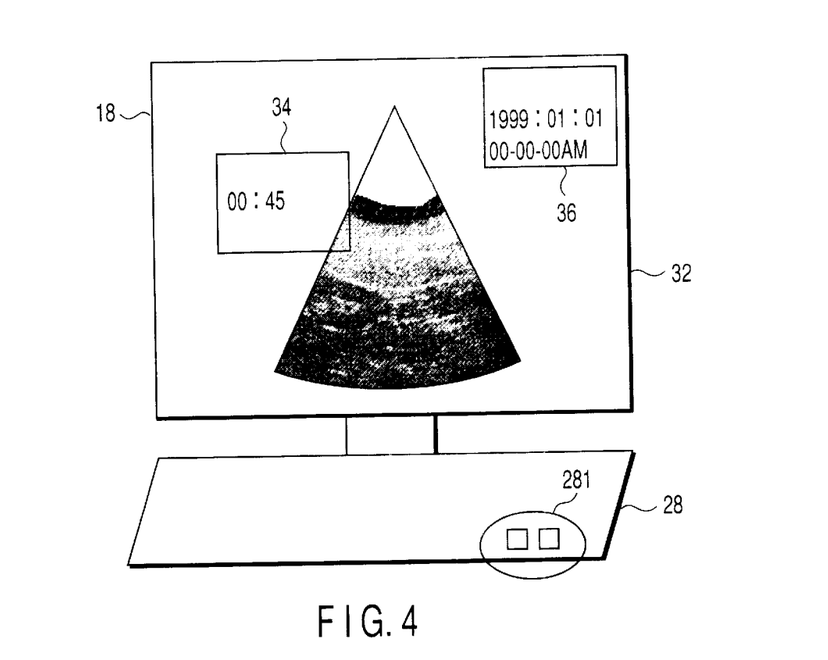
FIG. 4 is a view showing an image obtained by simultaneously displaying the time measured by an arbitrary time measuring circuit 26 and an ultrasonic image.

FIG. 4 is a view for explaining a frame image 32 obtained by simultaneously displaying the time measured by the arbitrary time measuring circuit 26 and the corresponding ultrasonic image within one frame. The elapsed time 34 is a measured time (elapsed time) after contrast medium administration. A date display 36 displays the date of imaging operation recorded by a timepiece incorporated in the ultrasonic image diagnostic apparatus 1. A stopwatch operation switch 281 is a switch for starting and stopping time measurement by the arbitrary time measuring circuit 26.

If the operator finds a desired frame, e.g., a frame showing the beginning of the production of an effect of the contrast medium, at time T1=00:45 (0 min 45 sec) in FIG. 3, while observing the frame image 32, he/she stores (captures) the image in the first storage section 20 by predetermined operation. That is, the frame image 32 shown in FIG. 4 is stored in the first storage section 20.

Continuously obtained images are displayed on the monitor 18 in real time. The operator can capture frame images for the desired subsequent period of time.

Subsequently, frame images are captured by a required number (FIG. 3 shows a case wherein the frame images at times T2, T3, T4, and T5 are captured). At time T5, the capturing operation is completed. At time T6, the operator presses the stopwatch operation switch 281 to stop the time measurement processing and terminate the capturing operation. Note that the total of five frame images, i.e., the images at times T1 to T5, may be captured such that only the capturing operation at time T1 is manually started, and capturing operation is automatically performed at equal intervals from time T1, instead of capturing all the images manually.

The following effects can be obtained according to the arrangement described above.

When time measurement is to be executing during diagnosis using an ultrasonic image diagnostic apparatus, an ultrasonic image and elapsed time can be simultaneously displayed as a frame image. This makes it possible to simplify the operation associated with time measurement and hence improve the operability.

When a desired ultrasonic image is to be captured, the ultrasonic image can be stored as a frame image, together with the measured time. This can omit the cumbersome operation of separately recording a contrast medium administration start time, elapsed time, and the like. Therefore, the operability can be improved.

In this embodiment, since the operator manually starts time measurement, he/she can obtain desired time information as measured time, e.g., "an elapsed time from contrast medium administration" or "an elapsed time from the start of image capturing".

Note that the ultrasonic image diagnostic apparatus 1 has the function of arbitrarily changing the position and size of the elapsed time 34 displayed on the monitor 18, and hence can change them to a desired position and size. The ultrasonic image diagnostic apparatus 1 also has the function of inhibiting the display of the elapsed time 34. If, therefore, no time measurement is required, the display of the elapsed time 34 can be eliminated.

The ultrasonic image diagnostic apparatus 1 shown in FIG. 2 is configured to separately set the host CPU 24 and arbitrary time measuring circuit 26. If, however, the host CPU can measure an arbitrary time, the host CPU may have the function of the arbitrary time measuring circuit 26.

Figure 5:
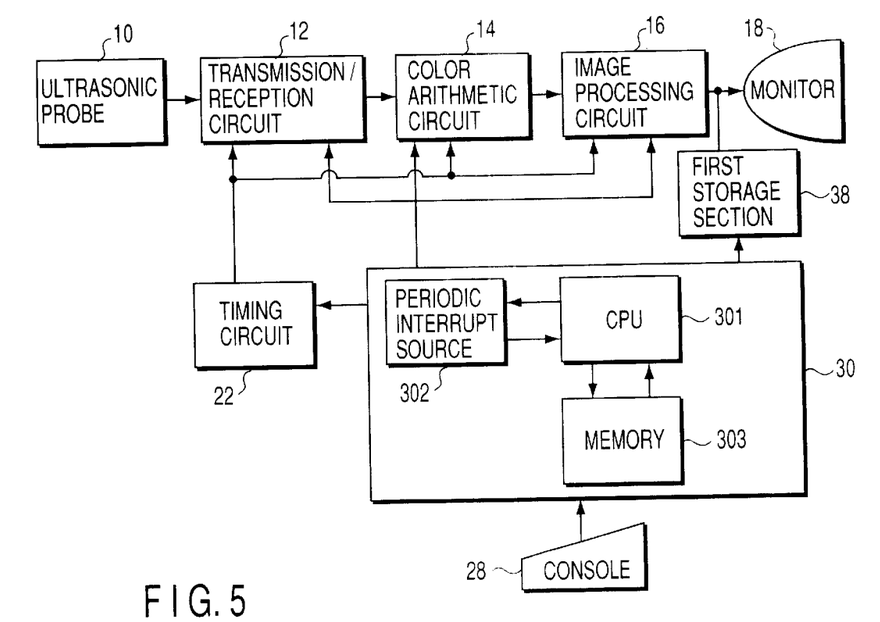
FIG. 5 is a block diagram showing the schematic arrangement of a modification of the ultrasonic image diagnostic apparatus according to the first embodiment.

FIG. 5 shows an ultrasonic image diagnostic apparatus 2 as a modification of the first embodiment, in which arbitrary time measurement is implemented by a host CPU 30. The same reference numerals as in FIG. 2 denote the same parts in FIG. 5.

The host CPU 30 includes a CPU 301, periodic interrupt source 302, and memory 303. The CPU 301 executes control associated with time measurement on the basis of a program stored in the memory 303. The periodic interrupt source 302 is a transmitter such as a pulse generator and exclusively used for arbitrary time measurement.

The CPU 301 counts interrupts from the periodic interrupt source 302 and performs time measurement in accordance with a program associated with the time measurement. Note that as the periodic interrupt source 302, an existing interrupt source represented by an RTC (Real Time Clock) can be used. In consideration of measurement errors, it is important that the intervals of interrupts from the periodic interrupt source 302 be sufficiently shorter than the minimum interval of time measurement.

The same effects as those described above can be obtained with this arrangement.

(Second Embodiment)

In the first embodiment, the first storage section 20 is configured to simultaneously store the time (elapsed time) measured by the arbitrary time measuring circuit 26 and the corresponding ultrasonic image for each frame image. In contrast to this, an ultrasonic image diagnostic apparatus 2 according to the second embodiment is configured to store a captured ultrasonic image and the elapsed time at the time of capturing in separate storage sections in correspondence with each other, and simultaneously display the elapsed time and ultrasonic image on a monitor 18 upon reading them from the storage sections. With this arrangement, the same effects as those in the first embodiment can be realized.

Figure 6:
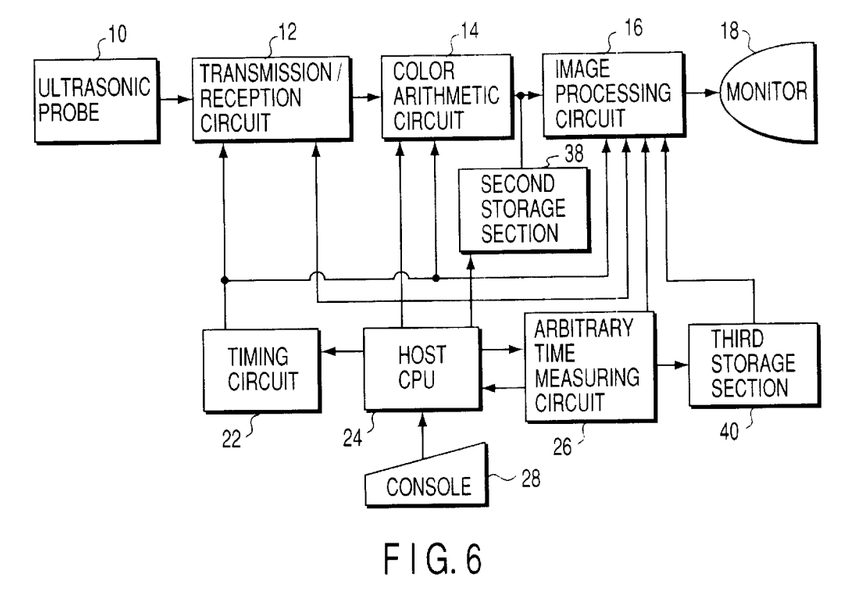
FIG. 6 is a block diagram showing the schematic arrangement of an ultrasonic image diagnostic apparatus according to the second embodiment.

FIG. 6 is a view showing the schematic arrangement of the ultrasonic image diagnostic apparatus 2 according to the second embodiment. The same reference numerals as in FIG. 2 denote the same parts in FIG. 6.

Referring to FIG. 6, a second storage section 38 is a storage section for storing an ultrasonic image on the basis of a capture instruction input by an operator with a console 28. The image stored in this storage section 38 has no image information attached thereto unlike the frame image stored in the first storage section 20 in the first embodiment. Management information, e.g., "first image with patient ID -" is attached to an ultrasonic image stored in the second storage section 38.

A third storage section 40 is a storage section for storing the elapsed time measured by an arbitrary time measuring circuit 26 in correspondence with the captured image on the basis of a capture instruction input by the operator with the console 28. This operation can be implemented by attaching the same management information as that of the ultrasonic image to the corresponding elapsed time information.

Operation to be performed when a desired ultrasonic image and corresponding elapsed time information are to be captured (stored) in imaging operation performed by the ultrasonic image diagnostic apparatus 2 having the above arrangement using the flash echo imaging method will be described with reference to FIG. 2. Note that the operation of simultaneously displaying an elapsed time and corresponding ultrasonic image is the same as that in the first embodiment.

Referring to FIG. 3, time measurement is started at time T0 as in the first embodiment. Assume that first image capturing operation is performed at time T1. In this case, the second storage section 38 stores the corresponding ultrasonic image as the first image under the control of a host CPU 24. At the same time, the third storage section 40 stores the measured time data from the arbitrary time measuring circuit 26 as a measured time in correspondence with the first image under the control of the host CPU 24.

At time T2, the second image and the second measured time linked to the second image are stored by predetermined capturing operation. Subsequently, the third image and third measured time at time T3, the fourth image and fourth measured time at time T4, and the fifth image and fifth time at time T5 are stored in the same manner as described above.

When the operator is to play and observe an ultrasonic image stored in the second storage section 38, he/she can read out the desired ultrasonic image and corresponding elapsed time information from the third storage section 40 on the basis of management information, and can be displayed as a frame image 32 shown in FIG. 4.

According to this arrangement, as in the first embodiment, when the operator wants to know an elapsed time during imaging operation by the ultrasonic image diagnostic apparatus, he/she can simultaneously display the ultrasonic image and elapsed time as a frame image. When a desired ultrasonic image is to be captured, the ultrasonic image can be stored as a frame image, together with the elapsed time. This makes it possible to simplify the operation associated with time measurement. Consequently, the operability can be improved.

(Third Embodiment)

The third embodiment will exemplify the case wherein the function associated with time measurement and another function are synchronized with each other in an ultrasonic image diagnostic apparatus. For example, a case wherein the operation of stopping time measurement by the arbitrary time measuring circuit 26 is synchronized with the operation of stopping imaging operation by ultrasonic scanning will be described.

Since the arrangement of the ultrasonic image diagnostic apparatus according to the third embodiment is the same as that shown in FIG. 2, and hence FIG. 2 will be referred to. Note that the time measurement start operation by an arbitrary time measuring circuit 26 and operations associated with image display and image capturing are the same as those in the first embodiment.

Assume that the operator inputs a signal for stopping imaging operation by ultrasonic scanning with a console 28 in FIG. 2. A host CPU 24 receives this input signal to stop the imaging operation by ultrasonic scanning, and performs control to stop the time measurement operation of the arbitrary time measuring circuit 26.

Note that synchronizing the function associated with time measurement with another function in this ultrasonic image diagnostic apparatus can also be implemented in the ultrasonic image diagnostic apparatus 2 according to the second embodiment.

According to this arrangement, the function associated with time measurement can be synchronized with another function. Since the operator need not operate a stopwatch operation switch 281, the third embodiment can further simplify the operation associated with time measurement to improve the operability, in addition to having the effects in the first or second embodiment.

(Fourth Embodiment)

The fourth embodiment will exemplify the case wherein the function associated with time measurement in an ultrasonic image diagnostic apparatus is synchronized with the function associated with an external device. A case wherein an automatic ultrasonic contrast medium administering unit 44 is taken as an example of the external device, and the start of contrast medium administration by the automatic ultrasonic contrast medium administering unit 44 is synchronized with the start of time measurement by an arbitrary time measuring circuit 26 in the ultrasonic image diagnostic apparatus will be described below.

Figure 7:
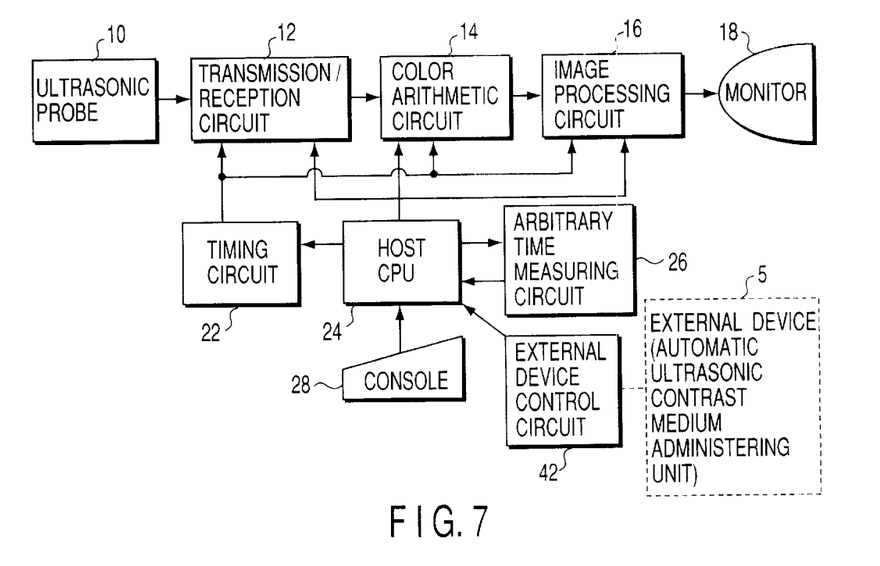
FIG. 7 is a block diagram showing the schematic arrangement of an ultrasonic image diagnostic apparatus according to the fourth embodiment.

FIG. 7 shows the schematic arrangement of an ultrasonic image diagnostic apparatus 4 according to the fourth embodiment.

The ultrasonic image diagnostic apparatus 4 further includes an external device control circuit 42 for synchronizing the function of an external device with the function of the ultrasonic image diagnostic apparatus 4, in addition to the respective components of the ultrasonic image diagnostic apparatus 1 according to the first embodiment. The external device is an automatic ultrasonic contrast medium administering unit 5 for automatically administering an ultrasonic contrast medium into an object with predetermined operation.

First of all, the operator instructs to administer an ultrasonic contrast medium with predetermined operation in the automatic ultrasonic contrast medium administering unit 5. Upon reception of an instruction from a CPU (not shown) of the automatic ultrasonic contrast medium administering unit 5, the external device control circuit 42 of the ultrasonic image diagnostic apparatus 4 instructs a host CPU 24 to start time measurement. An arbitrary time measuring circuit 26 receives a control signal from the host CPU 24 and starts time measurement.

The time measurement performed by the arbitrary time measuring circuit 26 is stopped in accordance with a stop instruction from the operator with a stopwatch operation switch 281. However, this stopping operation may be synchronized with input operation for re-administration of an ultrasonic contrast medium from the automatic ultrasonic contrast medium administering unit 5.

Note that as another example of the external device, a drug administering unit used in stress echo operation can be presented.

Synchronizing between the function associated with time measurement by this ultrasonic image diagnostic apparatus and the function of the external device can also be implemented in the ultrasonic image diagnostic apparatuses according to the first, second, and third embodiments.

According to this arrangement, since the function associated with time measurement by the ultrasonic image diagnostic apparatus can be synchronized with the function of an external device, the operation associated with time measurement can be further simplified, and the operability can be improved.

(Fifth Embodiment)

Recently, in the contrast echo method, many studies have been made on a quantitative analysis method for dynamic evaluation of bloodstream. For example, TIC (Time Intensity Curve) measurement is available. According to this technique, changes in luminance in an area of interest over time are plotted to quantitatively grasp the process of intensifying an echo signal in the area of interest.

The fifth embodiment will exemplify the ultrasonic image diagnostic apparatus for simultaneously displaying object function information like this TIC and a measured time (elapsed time) and storing them in correspondence with each other.

A TIC 35 is generated by an image processing circuit 16 on the basis of a plurality of ultrasonic images acquired by predetermined operation. The image processing circuit 16 also generates a table showing the correspondence between the time measured by the image processing circuit 16 and the abscissa (time) of the TIC 35, and stores the table in a memory (not shown).

Figure 8:
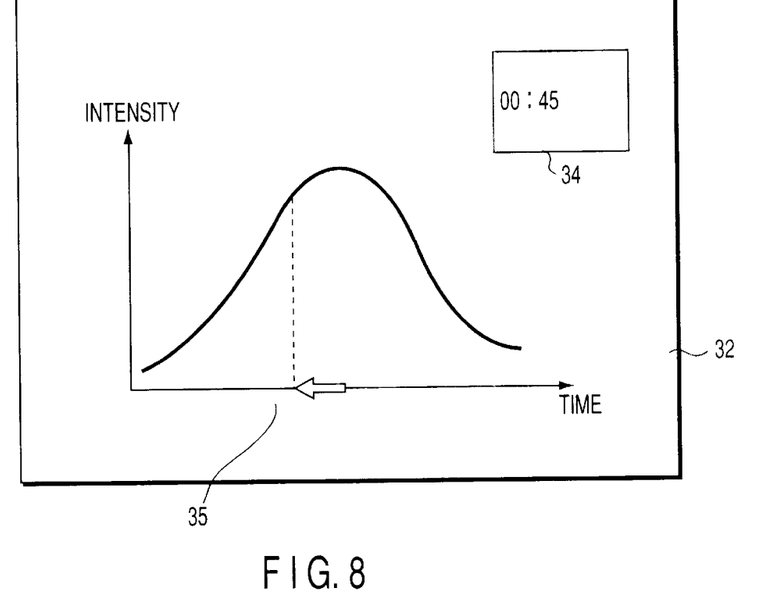
FIG. 8 shows an image 32 displaying the TIC 35 generated by the image processing circuit 16.

FIG. 8 shows an image 32 displaying the TIC 35 generated by the image processing circuit 16. The function implemented by the correspondence between a TIC and a measured time will be described with reference to FIG. 8.

Assume that the operator designates a time coordinate position indicated by the arrow in FIG. 8 with a pointer or the like. In this case, a host CPU 24 displays a measured time 34 corresponding to the coordinate position on a monitor 18 on the basis of the table. With this operation, the operator can easily grasp how much time had elapsed from contrast medium administration when the luminance designated on the TIC was measured. In addition, when the coordinate position to be designated is moved from the position indicated by the arrow in FIG. 8 by operation such as mouse dragging, the measured time changes in accordance with the movement, and the time corresponding to the finally fixed position is displayed.

The time measured by the image processing circuit 16 is stored in a third storage section 40 in correspondence with an ultrasonic image. Therefore, a TIC can be made to correspond to an ultrasonic image.

Figure 9:
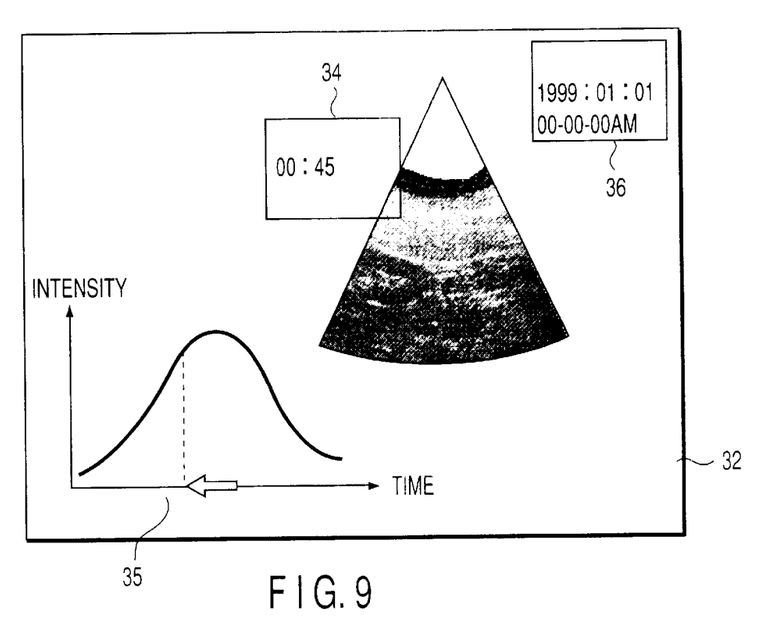
FIG. 9 shows an image 32 that simultaneously displays a TIC 35, ultrasonic image, and measured time 34.

FIG. 9 shows an image 32 that simultaneously displays a TIC 35, ultrasonic image, and measured time 34. The function implemented by the correspondence between a TIC, a measured time, and an ultrasonic image will be described with reference to FIG. 9.

Assume that the time coordinate position indicated by the arrow in FIG. 9 is designated by the operator with a pointer or the like. In this case, the host CPU 24 displays the measured time corresponding to the coordinate position on the monitor 18 on the basis of the correspondence table. The host CPU 24 reads out the ultrasonic image corresponding to the measured time from the third storage section 40 and displays it on the monitor 18. With this operation, the operator can easily grasp how much time had elapsed from contrast medium administration when the luminance designated on the TIC was measured. In addition, the operator can simultaneously observe the ultrasonic image at the time. Therefore, the operator can easily perform dynamic evaluation of bloodstream.

Note that when the operator designates a plurality of coordinate positions on the TIC 35, ultrasonic images and measured times 34 corresponding to the respective coordinate positions can be simultaneously displayed.

Figure 10:
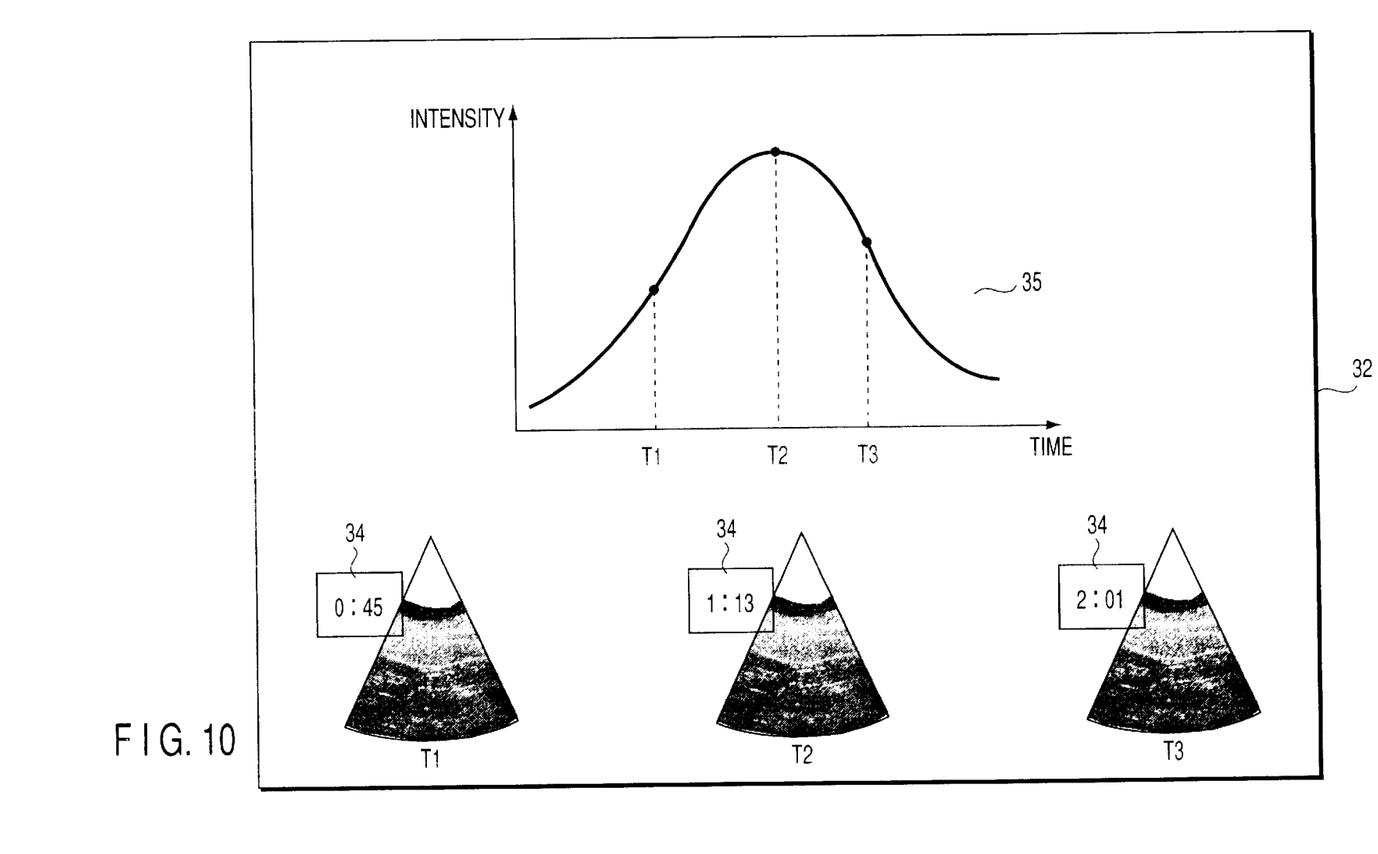
FIG. 10 shows an image 32 that simultaneously displays a plurality of ultrasonic images and measured times 34 with respect to one TIC 35.

FIG. 10 shows an image 32 that simultaneously displays a plurality of ultrasonic images and measured times 34 with respect to one TIC 35.

As shown in FIG. 10, when the operator designates three points, i.e., T1, T2, and T3 on a TIC, the measured times 34 and ultrasonic images corresponding to the respective points are displayed. The operator can therefore simultaneously observe changes in ultrasonic images at different time points on the TIC and elapsed times, and can easily perform dynamic evaluation of bloodstream.

The present invention has been described on the basis of the respective embodiments. However, the present invention is not limited to the above embodiments. For example, as indicated by (1) to (4), the respective embodiments can be variously modified without departing from the spirit and scope of the invention.

(1) In the first to fifth embodiments, elapsed times are displayed in number. However, the gist of the present invention is to simultaneously display measured times quantitatively, together with ultrasonic images or store them in correspondence with each other. The display of measured times is not limited to display in umber, and a measured time may be displayed with a hour hand or geometrically (e.g., an elapsed time is quantitatively displayed with the length of a line segment or a divided area of a circle). With this arrangement as well, the same effects as those described above can be obtained.

(2) In the first to fifth embodiments, time measurement is started from the start of contrast medium administration and the measured time is displayed, together with the ultrasonic image, or they are stored in correspondence with each other. The ultrasonic image diagnostic apparatus therefore has the stopwatch function. In contrast to this, even if the apparatus is configured to simultaneously display the time (date) of the start of contrast medium administration and the time (date) of image capturing, together with the ultrasonic image, or store them upon linking them to each other, by using the timepiece function provided in advance, necessary time information can be obtained. In this case, the apparatus is preferably configured to simultaneously display the elapsed time calculated from the time (date) of the start of contrast medium administration and the time (date) of image capturing or store it upon linking it to the above information.

(3) In the first to fifth embodiments, the image processing circuit 16 generates a synthetic image (frame image) of an ultrasonic image and elapsed time, and displays it as a frame image on the monitor 18. However, an elapsed time information need not always be synthesized with an ultrasonic image in the image processing circuit 16 and may be independently and directly displayed on the monitor 18. With this arrangement, the same effects as those described above can be obtained.

(4) It is preferable that the time measurement performed by the arbitrary time measuring circuits 26 and 24 be automatically reset for each patient. More specifically, reset operation may be performed when a patient ID or the like is input at the start of diagnosis. This arrangement can prevent operation errors such as confusion between time information about a given patient and that about another patient.

In executing a plurality of measurements consecutively, it is preferable that the time measurement performed by the arbitrary time measuring circuits 26 and 42 be automatically reset every time each measurement is completed. According to this arrangement, an elapsed time unique to each measurement can be acquired, and hence the operability can be improved.

According to the present invention, since the apparatus has the time measurement function, a measured time and an ultrasonic image can be simultaneously displayed or stored in correspondence with each other. This makes it possible to omit the cumbersome operation of independently recording a time and improve the operability.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus comprising:

an image generator configured to generate an ultrasonic image by scanning an inside of an object with an ultrasonic wave;

a time information generator configured to measure an elapsed time from a predetermined time that is during an administration of an ultrasonic contrast medium or to generate information from which the elapsed time can be derived; and a memory configured to store the ultrasonic image in association with the elapsed time or the information from which the elapsed time can be derived.

2. The apparatus of claim 1, further comprising:

a display configured to display the elapsed time or the information from which the elapsed time can be derived and the ultrasonic image, simultaneously.

3. The apparatus of claim 1, wherein:

said memory stores an image obtained by synthesizing the elapsed time or the information from which the elapsed time can be derived with the ultrasonic image into one frame.

4. An ultrasonic diagnostic apparatus comprising:

an image generator configured to generate an ultrasonic image by scanning an inside of an object with an ultrasonic wave;

a time information generator configured to measure an elapsed time from a predetermined time or to generate information from which the elapsed time can be derived;

a memory configured to store the ultrasonic image in association with the elapsed time or the information from which the elapsed time can be derived; and a controller configured to synchronize control associated with a start, pause, and stop of measurement of the elapsed time or the information from which the elapsed time can be derived with control associated with imaging or storage of an ultrasonic image.

5. An ultrasonic diagnostic apparatus comprising:

an image generator configured to generate an ultrasonic image by scanning an inside of an object with an ultrasonic wave;

a time information generator configured to measure an elapsed time from a predetermined time or to generate information from which the elapsed time can be derived;

a memory configured to store the ultrasonic image in association with the elapsed time or the information from which the elapsed time can be derived; and a controller configured to synchronize control associated with a start, pause, and stop of measurement of the elapsed time or the information from which the elapsed time can be derived with control associated with an external device.

6. An ultrasonic diagnostic apparatus comprising:

an image generator configured to generate an ultrasonic image by scanning an inside of an object with an ultrasonic wave;

a time information generator configured to measure an elapsed time from a predetermined time or to generate information from which the elapsed time can be derived; and a memory configured to store the ultrasonic image in association with the elapsed time or the information from which the elapsed time can be derived;

when said ultrasonic diagnostic apparatus obtains information associated with a new object, said time information generator starts after resetting, measuring a new elapsed time from a predetermined time point or generating information from which the new elapsed time can be derived.

7. An ultrasonic diagnostic apparatus comprising:

an image generator configured to generate an ultrasonic image by scanning an inside of an object with an ultrasonic wave;

a time information generator configured to measure an elapsed time from a predetermined time that is during an administration of an ultrasonic contrast medium or to generate information from which the elapsed time can be derived; and a memory configured to store function information of the object in association with the elapsed time or the information from which the elapsed time can be derived.

8. The apparatus of claim 7, further comprising:

a display configured to display the elapsed time or the information from which the elapsed time can be derived and the function information of the object, simultaneously.

9. The apparatus of claim wherein:

said memory stores an image obtained by synthesizing the elapsed time or the information from which the elapsed time can be derived and the function information of the object into one frame.

10. An ultrasonic diagnostic apparatus comprising:

an image generator configured to generate an ultrasonic image by scanning an inside of an object with an ultrasonic wave;

a time information generator configured to measure an elapsed time from a predetermined time or to generate information from which the elapsed time can be derived; and a memory configured to store function information of the object in association with the elapsed time or the information from which the elapsed time can be derived;

when said ultrasonic diagnostic apparatus obtains information associated with a new object, said time information generator starts after resetting, measuring a new elapsed time from predetermined time point or generating information from which the new elapsed time can be derived.

* * * * *